United States Patent [19]

Lembke et al.

[11] 4,246,256

[45] Jan. 20, 1981

[54] ORAL OR EDIBLE COMPOSITIONS

[76] Inventors: Andreas Lembke, Institut für Virusforschung und experimentelle Medizin, 2420 Eutin-Sielbeck; Dietrich Gorny, Wienerstrasse 75, 6000 Frankfurt am Main, both of Fed. Rep. of Germany

[21] Appl. No.: 6,307

[22] Filed: Jan. 24, 1979

[30] Foreign Application Priority Data

Jan. 31, 1978 [DE] Fed. Rep. of Germany ....... 2804138

[51] Int. Cl.³ .................... A61K 7/28; A61K 37/48
[52] U.S. Cl. ........................................ 424/50; 424/94
[58] Field of Search ............ 424/48, 49, 50, 94, 424/180, 343; 426/361, 548, 658, 660,

[56] References Cited

U.S. PATENT DOCUMENTS

| | | | |
|---|---|---|---|
| 3,075,884 | 1/1963 | Bilotti et al. | 424/48 |
| 3,194,738 | 7/1965 | Harrison et al. | 424/48 |
| 3,574,824 | 4/1971 | Echeandia et al. | 424/50 |
| 3,751,561 | 8/1973 | Wildi et al. | 424/48 |
| 3,914,434 | 10/1975 | Bohni | 424/343 |
| 4,082,841 | 4/1978 | Pader | 424/50 |
| 4,107,291 | 8/1978 | Ishibashi | 424/48 |
| 4,133,875 | 1/1979 | Hillman | 424/50 X |
| 4,150,113 | 4/1979 | Hoogendoorn et al. | 424/50 |
| 4,153,732 | 5/1979 | Muhler | 426/72 |
| 4,157,386 | 6/1979 | La Rochelle | 424/52 |

FOREIGN PATENT DOCUMENTS

| | | | |
|---|---|---|---|
| 751739 | 11/1970 | Belgium | 424/50 |
| 753877 | 12/1970 | Belgium | 424/50 |
| 756289 | 3/1971 | Belgium | 424/50 |
| 1927411 | 12/1970 | Fed. Rep. of Germany | 424/50 |
| 1033229 | 6/1966 | United Kingdom | 424/50 |
| 1270200 | 4/1972 | United Kingdom | 424/50 |

*Primary Examiner*—Shep K. Rose
*Attorney, Agent, or Firm*—Sughrue, Rothwell, Mion, Zinn and Macpeak

[57] ABSTRACT

Edible or oral compositions which limit the development of tooth decay and comprise lactate dehydrogenase. Included among such compositions are foods containing 0.1 to 2% of water and either sugar or sugar substitutes. Foods without sugar and pharmaceutical preparation are also included in the scope of this invention.

27 Claims, No Drawings

ORAL OR EDIBLE COMPOSITIONS

This invention relates to oral or edible compositions and their manufacture. It is particularly directed to food containing sugar and very little water and to pharmaceutical preparations, in particular hygiene agents for tooth and mouth care, containing little water.

It is known that in the oral cavity foodstuffs, beverages and medicaments with a high sugar content lead, in the presence of micro-organisms, to the formation of so-called "plaques" and acid decomposition products which severely attack tooth enamel. This effect is known by the name caries. Caries is understood to be an initial attack on the surface of teeth which are then progressively destroyed by cavities being formed therein.

Those micro-organisms which are not present in or under the films on teeth, called plaques, are of prime importance for the development of dental caries. As with all other germs present in the oral cavity, the micro-organisms present in the dental plaques live on the food residues remaining in the mouth after the intake of food. Low-molecular carbohydrates, above all various types of sugars, are particularly acceptable to the bacteria because they are the best sources of energy for the intensive growth and metabolism processes of the bacteria.

The mechamism of the formation of caries does not yet appear to be fully understood. The cariogenic microbes, for example Streptococcus mutans, form the ferment dextran saccharase which breaks sucrose down into anhydroglucose and fructose. The anhydoglucose molecules can then accumulate, forming polymeric molecules which are called dextran gels. Amongst these, especially those dextran gels with a molecular weight of 10,000 to 200,000 have a particular adhesion. These dextran gels serve to a certain extent as "adhesives" which hold the bacteria concerned firmly on the surfaces of the teeth, that is to say which form plaques. Under the plaques and with exclusion of air, the bacteria mentioned can then produce, for example from sugar which has diffused in, acid, such as for example, lactic acid or other acids which destroy teeth, and this lead to the formation of first lesions of the enamel (initial caries), that is to say corrosion of the dentine, with the known, consequential, results. After the plaques have formed, calcium and phosphate are gradually dissolved out, especially from the apatite of tooth enamel, under the action of acid during the carious demineralisation taking place under the plaques.

Two directions have been adopted in attempts made hitherto to inhibit caries. These consist, in principle, of either increasing the resistance of the hard substance of teeth to attack by acid or of weakening the attack on the teeth by acid.

The first-mentioned solution to the problem includes experimental fluoridation of drinking water, salt or milk, which has been carried out on a large scale in the USA and in Switzerland. Furthermore, local application of fluoride-containing tablets and the use of fluorinated compounds, such as sodium fluoride, sodium monofluorophosphate, tin fluoride/calcium pyrophosphate or amine fluoride, may also be mentioned. Although, according to reports, a decrease in carious lesions by this means has been reported (sic) the results achieved are still unsatifactory. Moreover, there are considerable reservations, also of a physiological nature, against introducing chemicals into, in particlar, drinking water and foodstuffs such as milk. In addition, with the present diet of the civilian population, collective and individual fluoridation measures are not sufficient to counteract carious decay of teeth.

Attempts have also been made, however, to combat caries by controlling the formation of dextran, for example by the action of chemicals. The use of sodium oleate and linoleate for this purpose has been described, in "Journal of Dental Health", volume 22, No. 4, December 1972, for example. The action of the sodium oleate and linoleate, according to German Offenlegungsschrift No. 2,442,825 on the formation of dextran, is said to be further increased by water-soluble secondary phosphates in agents for dental hygiene. The use of Ca salts, Na salts or Mg salts of esters of phosphoric acid with sucrose, glucose or lactose for the manufacture of dental hygiene products having a cariostatic action in the oral cavity has also been considered in German Auslegeschrift No. 1,467,809. These measures of blocking the metabolism of microflora in the mouth, which use the dextran/sucrose/enzyme system for producing the dental plaques have indeed brought about a certain improvement of dental hygiene agents, but have not brought about the desired decisive combating of carious tooth decay.

The known attempts to utilise the lyolysis principle, that is to say to prevent caries either by destroying the cariogenic micro-organisms by complete or partial disintegration, or by complete or partial disintegration of the adhesive dextran gels, have also hitherto been unsatisfactory. Accordingly, the destruction of or attack on cariogenic microbes by enzymes which have been isolated from certain strains of Streptococci is disclosed in German Auslegeschrift No. 2,011,935. Three defined strains and their incorporation into dental hygiene agents have been given for this purpose. Moreover, the lyolysis principle has also been applied to dextran which has already been formed using the enzyme dextranase according to German Offenlegungsschrift No. 1,955,956. Nevertheless, according to EURATOM (sic) Pat. No. 318,815, the dextranase was capable of decomposing only soluble dextran, since insoluble dextran contains a proportion of mutan (sic) which cannot be attached by dextranase. The use of "mutanase" has therefore been proposed in this Austrian Publication.

However, these attempts to improve dental hygiene agents by the disintegration of the micro-organisms producing dextran or the dextrans themselves and to incorporate systems of this type in dental hygiene agents also have not hitherto been completely satisfactory. This is partly attributable to the fact that it is not always possible to clean the teeth after each meal or after sweets and the like have been eaten, in order to stop the damage occuring in the meantime.

Replacing some or all of the sucrose by other, non-cariogenic sugars or sugar alcohols or by artificial sweeteners was envisaged as a further way of combating caries.

In many applications, complete replacement of sucrose by sugar substitutes which have a low cariogenic action or are non-cariogenic, for example by the sugar alcohols xylitol and sorbitol, is not possible for technological, economic, organoleptic or medical reasons.

Amongst the artificial sweeteners, saccharin, one of the best known and most frequently used sugar substitutes, has the disadvantage that it produces an aftertaste which is unpleasant to the consumer. The medical profession is making known their serious reservations with regard to the harmful nature of other substances, for example that cyclamates. On the other hand, artificial sweeteners have the disadvantage that, because of the high sweetening power, the small amounts to be used are not easy to meter, for example an "empty taste" is spoken of in this connection, that is to say the desired "body" is missing. Physiological effects also hamper general use of these artificial sweeteners.

The use of enzymes to accelerate the decomposition of food residues and thereby to prevent the formation of plaques has also been recommended. α-Glucosidases and/or β-fructosidases (German Offenlegungsschrift No. 1,927,411), and a polymer-enzyme compound which contains neutral, alkaline and acid proteases, in addition to amylse (sic), lipase and dextranase (German Offenlegungsschrift No. 1,948,298), are mentioned.

In spite of these numerous attempts to combat caries, which are based on the most diverse principles, there still exists the urgent need for additional or improved measures for preventing the harmful results of attack by acid in the presence of cariogenic micro-organisms in order to make suppression of caries possible in the case of a conventional diet.

An object of the present invention is to counteract the harmful effects of caries both by improving conventional foodstuffs of low water content, which have been prepared using sugars, and optionally in addition by simultaneously improving dental hygiene agents and pharmaceutical preparations. The improvement of foodstuffs should particularly take into account the fact that the cariogenic attack takes place in the intervals of time between the customery periods of cleaning the teeth. In particular, it is intended, according to the invention, to convert foodstuffs into foodstuffs "which are not harmful to teeth" by adding a physiologically acceptable substance, with or without complete replacement of the sugars customarily used for this.

According to the present invention there is provided an oral or edible composition which composition contains sugar, sugar substitutes or no sugar and very little water and having a content of lactate dehydrogenase which limits promotion of tooth decay.

Surprisingly, it has been found in experiments that carious attack is greatly decreased by the addition of the enzyme lactate dehydrogenase. It is assumed that by this additon of lactate dehydrogenase, an inhibition system is incorporated into foodstuffs and confectionery of low water content or containing no water, and when these products are eaten, this system counteracts the harmful effect, in the presence of cariogenic bacteria, of the products formed by the decompostion of sugars, and converts the foodstuffs, in particular confectionery.

Foodstuffs "of low water content" are those foodstuffs with a very low moisture content. By this there are preferably understood foodstuffs with a residual moisture of 0.1 to 2%.

Suitable "sugar-containing" foodstuffs of the present invention are those which contain a proportion of naturally occurring sugars, such as sucrose, glucose, fructose and the like. Foodstuffs containing sucrose are particularly preferred. It is known that in the case of certain foodstuffs of low water content, sucrose has considerable technological advantages compared with other types of sugars. Foodstuffs containing sugar alcohols as sugar substitutes, and foodstuffs containing no sugar are included in the present invention.

If appropriate, even such foodstuffs or confectionery or pharmaceutical preparations which contain no customery sugars or which are essentially sugar-free can be used. These can be materials which are sweetened on the basis of sugar substitutes, for example with saccharin, cyclamate, protein sweeteners extracted from tropical plants, xylitol and the like. However, they can also be products which naturally contain essentially no sugar constituent and also do not require significant sweetening. It is also advantageous to incorporate lactate dehydrogenase into the type of confectionery. When the foodstuff is eaten, a proportion of this additive can in fact remain in the oral cavity together with the food residues adhering to the teeth and can there render harmless, for example, cariogenic products resulting from decomposition of carbohydrates.

The expression "sugar-containing foodstuffs of low water content", however, is intended to comprise, in particular, confectionery. Examples of confectionery or closely related products are bakery products, desserts and artificial honey. Products of particular interest are so-called stimulants, such as various types of sweets, that is to say hard and soft toffees (bonbons), fondant, meringue wares, gum-type confectionery, liquorice, dragees, fruit pastes, nut caramel, effervescent powders, marzipan, persipan, (a marzipan substitute made from peach or apricot kernals), nougat, chocolates and coco products, lollipops, pastilles, chewing gum and the like. Products of the chewing gum type are particularly interesting, since such products are in contact with saliva for a long time and have a long residance time in the mouth. Although chewing gums are not usually swallowed, they are nevertheless regarded as foodstuffs in this context and thus fall within the concept of the invention.

Long-term contact in connection with relatively long residance times are understood as times of at least several minutes in the case of the products to be administered orally.

According to the invention, the foodstuff can also be an animal feed.

According to another embodiment of an oral or edible composition of the invention, lactate dehydrogenase is added to pharmaceutical preparations as the active compound which can, of course, also be additionally present alongside other customary active compounds. Possible pharmaceutical preparations of this type are, above all, tablets and degrees, which contain sugars, in addition to substances having a pharmacological action. Products which may be mentioned to which the invention is applicable are various types of so-called quasi-medicinal products, such as, for example, cough mixtures or syrups and the like. Such products are frequently taken before going to bed, that is to say after the teeth have already been brushed, and thus have a long-term action on the film on the teeth.

Mouth hygiene tablets in the broadest sense, such as dental hygiene dragees and tablets for chewing, and tooth-cleansing chewing gums are a preferred pharmacuetical preparation (sic) within the scope of the invention. In this case also, the advantageous action of the active compound is based on the fact that because of insalivation in the oral cavity, an enzymatic protective film which is able to prevent the conversion of any residues of sugars present into cariogenic products can cover the teeth.

The dental hygiene agents mentioned can be, for example, in the form of a dental tablet which contains the customary polishing agents, binders, thickeners and humectants.

Examples of suitable polishing agents which can be used, for example, for detal hygiene agents are the customary calcium phosphates, such as tricalcium phosphate, alkali metal methaphosphate (sic), magnesium carbonate, pulverulent plastics, such as polymethyl methacrylate, urea/formaldehyde condensation products and the like, or mixtures of such substances.

In addition, the dental hygiene agents can also contain preservatives, aroma substances and other auxiliaries. In individual cases, however, it can also be desirable to assist or multiply the action of other active compounds, the aim of which is caries protection on the basis of other principles, by adding lactate dehydrogenase. Such customery active compounds which may be mentioned are, in particular, fluorine compounds, such as amine fluorides, alkali metal fluorides and the like, or dextranases.

The enzyme lactate dehydrogenase (also designated LDH in the following text) used according to the invention is commerically available. Lactate dehydrogenase can also be manufactured, inter alia, from various microbes, for example yeast. The LDH obtained from yeast is relatively stable, for example an enzyme preparation dissolved in glycerol remains active at $+18°$ C. for over one year. Moreover, LDH can also be stored for a relatively long time in buffer solutions within a defined pH range without an appreciable loss in activity. As experiments within the scope of the invention have shown, LDH incorporated in foodstuffs or pharmaceutical preparations of low water content or containing no water suffers only a relatively small loss in activity during customary storage times, if any loss occurs at all.

The amount of lactate dehydrogenase which is incorporated into the foodstuff, the confectionery or the pharmaceutical preparation, such as tooth-cleansing tablets, but in particular in hygiene agents in tablet form for dentures, can easily be determined by the expert on the basis of the specific enzyme activity, the approximate sugar content of the material, if there is one, and on the basis of the pH range in the binder or existing during its manufacture.

According to the invention, it is preferable to choose the amount of enzyme activity incorporated, according to the storage time to be assumed for the material, so that, at the moment of eating, this is at least about adequate to cause the desired effect.

In general, an LDH amount of 0.2 mg to 0.5 g/kg is suitable. 0.5 mg–0.05 g/kg, relative to a specific activity of about 300 U/mg. is preferably used.

In addition, the temperature and if appropriate the water content of the material on adding the enzyme and its customary storage temperature are also to be taken into consideration. The proportion of enzyme which is appropriately to be incorporated can be determined by simple experimental batches.

It also applies to pharmaceutial preparations, and in particular dental hygiene agents or mouth hygiene agents, into which lactate dehydrogenase can be incorporated, that the amount of enzyme to be incorporated is determined by rough calculations or empirical experiments. In dental hygiene agents and mouth hygiene agents of this type, there is usually no sugar content, for which reason it is not necessary to orientate the enzyme activity to be incorporated with respect to this sugar content. In this case, incorporation of the enzyme has the purpose of producing a caries-inhibiting liquid film in the oral cavity, especially on the teeth, so that any food residues remaining, which are not removed even by brushing, cannot lead to caries in the presence of cariogenic bacteria.

Intensification of the lactate dehydrogenase action by adding a suitable hydrogen acceptor, for example nicotin-amide-adenine dinucleotide, is also envisaged according to the invention.

The incorporation of the enzyme lactate dehydrogenase is appropriately carried out in a manner such that a homogeneous distribution within the foodstuff results. On the other hand, it is also preferable, especially if the foodstuff itself contains no isotropic distribution of sugar, likewise to provide a non-uniform distribution of the enzyme incorporated. Thus, for example, in the case of chocolate mixed with whole nuts, it would not be necessary to homogeneously mix the nut constituent of the chocolate with the enzyme.

The incorporation of lactate dehydrogenase is usually carried out at a pH value at which this enzyme is stable, and at a temperature at which the enzyme is not denatured. A prefered pH range is between pH 5 and 7. It is particularly preferable to incorporate the LDH into the foodstuff and the like at the pH value of optimum stability of the enzyme. Suitable incorporation temperatures for LDH are between 0° and 50° C., and temperatures between 20° and 50° C. are to be regarded as particularly favourable. The temperature range from 20° to 40° C. is particularly preferred, depending on the intended use.

It can be desirable, depending on the nature of the medium, to add the enzyme either in the course of the manufacturing process or after finishing the foodstuff or the pharmaceutical preparation. In the case of confectionery such as chocolate bars, chocolates and the like, it is preferable to add the enzyme only at a relatively late point in time so that no losses in activity during the course of the production of the confectionery result.

In the following text, experiments are described which demonstrate the anti-cariogenic action when lactate dehydrogenase is added:

A commercially available, fat-containing and sugar-containing spread of low water content was used as the cariogenic substrates. While, homozygous rats of the "Wistar" type were used as the experimental animals. The spread mentioned was admixed in an amount of 50% of the total amount to a standard dry feed (Herilan-RM 20), consisting of a vitamin-rich protein/fat diet which has been developed taking into consideration all the metabolism requirements of rats.

The air-dried experimental diet was proportioned and metered so that the animals could further increase in weight during the feedingperiod of 280 days. The animals were kept in plastic cages which were each provided with drinking and feeding machines. 50 to $60 \times 10^3$ Streptococci (sic) mutans germs per milliliter were added to the drinking water in each case at intervals of 30 days. Sterilised fine wood granules which were replaced at intervals of 36 hours were used as the litter. The room was air-conditioned.

The animals were divided into experimental groups consisting of 60 animals each. All the animals were inspected daily and weighed at intervals of 30 days, during which no side-effects at all from the content of LDH could be detected.

The appearance of caries, in particular of carious lesions, was established by means of a stereomicroscope with a magnification of 12:

The following gradings were recorded.
0 = no caries
1 = 1 to 5 lesions
2 = 5 to 10 lesions
3 = more than 10 lesions.

The following diet compositions were tested:
A = 50% of dry feed + 50% of spread;
B = 50% of dry feed + 50% of spread + lactate dehydrogenase.

The amount of lactate dehydrogenase was 0.5 mg/kg of spread.

When the rats were fed with diet A, numerous carious lesions occured: a total of 30 (50%) of the experimental animals was affected. The experimental results with regard to the number of lesions and also the degree of severity in each case are summerized in the table which follows. As the results show, carious attack which in some cases was very severe (>10 lessions) was found in the experimental animals fed with diet A. In the case of diet B, both the number and the degree of severity of the lesions were considerable reduced by adding LDH. This clearly shows the effect, which is not harmful to teeth, of the diet provided with LDH.

TABLE

| Experimental group | Caries lesions (number × degree) |
|---|---|
| A (diet A) | 15 × 1; 9 × 2; 6 × 3 |
| B (diet B) | 6 × 1; 3 × 2 |

Further examples of a foodstuff and a pharmaceutical preparation which contain a lactate dehydrogenase additive are given in the following text.

1. Milk chocolate bar

| | | |
|---|---|---|
| con-<br>tain-<br>ing | cocoa paste | 26 g |
| | sucrose | 60 g |
| | milk fat | 3.2 g |
| | fat-free dry substance and lactate dehydrogenase, which was stirred in, to form a homogeneous distribution, at about 40-45° C. before cooling the finished chocolate | 9.5 g<br><br><br><br><br><br>5-10 mg |

2. Tooth-cleansing dragee

| | | % by weight |
|---|---|---|
| con-<br>tain-<br>ing | magnesium cargonate | 10.0 |
| | silicon dioxide | 20.0 |
| | dicalcium phosphate | 55.0 |
| | a urea/formaldehyde condensate | 5.80 |
| | aroma substances | 2.0 |
| | tragacanth | 1.5 |
| | sodium lauryl-sulphoacetate | 2.5 |
| | a long-chain amine fluoride | 2.0 |
| | lactate dehydrogenase | 0.01 |

What we claim is:

1. An oral or edible low moisture content composition which composition contains sugar, sugar substitutes or no sugar and lactate dehydrogenase in an amount sufficient to limit promotion of tooth decay.

2. A composition according to claim 1 which contains saccharose.

3. A composition according to either of claims 1 or 2 in which the lactate dehydrogenase is included in an amount sufficient to prevent the formation of cariogenic decomposition products or of products promoting caries.

4. A composition according to either of claims 1 or 2 which further contains a suitable hydrogen acceptor in an amount sufficient to intensify the effects of the content of lactate dehydrogenase.

5. A composition according to any one of claim 1 or 2 which is a food.

6. A composition according to any one of claim 1 or 2 which is a pharmaceutical composition for tooth or mouth care.

7. A method for the production of an oral or edible low moisture content composition which contains sugar, sugar substitutes or no sugar and wherein lactate dehydrogenase is added to the composition during or after the production of the composition in an amount sufficient to limit promotion of tooth decay.

8. A method according to claim 7 wherein the lactate dehydrogenase is introduced into the composition to achieve a homogeneous distribution.

9. A method according to either of claim 7 or 8 wherein the composition is kept at pH-values of optimal enzyme stability during the time the lactate dehydrogenase is added.

10. A method according to claim 9 wherein the composition is kept at a pH of from 4 and 7 during the time the lactate dehydrogenase is added.

11. A method according to any one of claims 7 or 8 wherein the composition is kept at a temperature of from 20 and 50 degrees Centigrade during the time the lactate dehydrogenase is added.

12. A method according to one of claims 7 or 8 wherein a suitable hydrogen acceptor is added in an amount sufficient to intensify the effects of the lactate dehydrogenase.

13. A composition according to claim 3 which further contains a suitable hydrogen acceptor in an amount sufficient to intensity the effects of the contents of lactate dehydrogenase.

14. A composition according to claim 3 which is a food.

15. A composition according to claim 4 which is a food.

16. A composition according to claim 3 which is a pharmaceutical composition for tooth or mouth care.

17. A composition according to claim 4 which is a pharmaceutical for tooth or mouth care.

18. A method according to claim 8 wherein the composition is kept at a temperature of from 20° and 50° C. during the time the lactate dehydrogenase is added.

19. A method according to claim 10 wherein the composition is kept at a temperature of from 20° and 50° C. during the time the lactate dehydrogenase is added.

20. A method according to claim 9 wherein a suitable hydrogen acceptor is added in an amount sufficient to intensify the effects of the lactate dehydrogenase.

21. A method according to claim 10 wherein a suitable hydrogen acceptor is added in an amount sufficient to intensify the effects of the lactate dehydrogenase.

22. A method according to claim 11 wherein a suitable hydrogen acceptor is added in an amount sufficient to intensity the effects of the lactate dehydrogenase.

23. A composition according to claim 1 wherein the lactate dehydrogenase is included in an amount of about 0.2 mg to 0.5 g per kg of composition.

24. A composition according to claim 1 wherein the lactate dehydrogenase has a specific activity of about 300 U/mg and is included in an amount of about 0.5 mg to 0.05 g per kg of composition.

25. A composition according to claim 1 which further contains nicotin-amide adenine dinucleotide as a hydrogen acceptor.

26. A composition according to claim 1 which is a milk chocolate bar comprising cocoa paste, sucrose, milk fat and lactate dehydrogenase in an amount sufficient to limit the promotion of tooth decay.

27. A compositon according to claim 1 which is a tooth-cleansing dragee magnesium cargonate, silicon dioxide, dicalcium phosphate, a urea-formaldehyde condensate, a long-chain amine fluoride and lactate dehydrogenase.

* * * * *